US011075010B1

(12) United States Patent
Goswami et al.

(10) Patent No.: US 11,075,010 B1
(45) Date of Patent: Jul. 27, 2021

(54) PHARMACOLOGY MODEL OPTIMIZATION BASED ON DISTRIBUTED DATA ACQUISITION

(71) Applicant: Insight RX, Inc., San Francisco, CA (US)

(72) Inventors: Srijib Goswami, Walnut Creek, CA (US); Ron Keizer, Lafayette, CA (US); Ranvir Mangat, San Francisco, CA (US)

(73) Assignee: Insight RX, Inc., San Francisco, CA (US)

( * ) Notice: Subject to any disclaimer, the term of this patent is extended or adjusted under 35 U.S.C. 154(b) by 0 days.

(21) Appl. No.: 16/824,109

(22) Filed: Mar. 19, 2020

(51) Int. Cl.
  *G16H 50/70* (2018.01)
  *G16H 70/40* (2018.01)
  *G16H 10/40* (2018.01)
  *G16H 10/60* (2018.01)
  *G16H 50/50* (2018.01)
  *G06F 30/20* (2020.01)
  *A61B 5/00* (2006.01)
  *G16H 20/10* (2018.01)
  *A61B 5/145* (2006.01)

(52) U.S. Cl.
  CPC .......... *G16H 50/70* (2018.01); *A61B 5/4848* (2013.01); *G06F 30/20* (2020.01); *G16H 10/40* (2018.01); *G16H 10/60* (2018.01); *G16H 20/10* (2018.01); *G16H 50/50* (2018.01); *G16H 70/40* (2018.01); *A61B 5/14546* (2013.01)

(58) Field of Classification Search
  CPC ........ G16H 50/70; G16H 50/50; G16H 10/40; G16H 10/60; G16H 70/40; G16H 20/10; G06F 30/20; A61B 5/4848; A61B 5/14546

USPC .......................................................... 705/2–3
  See application file for complete search history.

(56) References Cited

U.S. PATENT DOCUMENTS

| 10,083,400 | B2 | 9/2018 | Mould | |
|---|---|---|---|---|
| 2004/0023211 | A1* | 2/2004 | Groen | G16H 20/10 435/5 |
| 2009/0006129 | A1* | 1/2009 | Thukral | G16H 20/10 705/2 |

(Continued)

OTHER PUBLICATIONS

U.S. Appl. No. 61/710,330, filed Oct. 5, 2012.

*Primary Examiner* — Jason S Tiedeman
*Assistant Examiner* — Rachel F Durnin
(74) *Attorney, Agent, or Firm* — Cognition IP, P.C.; Edward Steakley (57) ABSTRACT

Methods, systems, and apparatus, including computer programs encoded on computer storage media for pharmacology model optimization based on distributed data acquisition. A computer system stores a first pharmacology model associated with a drug dosage model for a particular medication. The computer system receives patient data including pharmacological data and data values for a drug identifier and a pharmacology model identifier. The pharmacological data being associated to drug dosing for the particular medication. The computer system aggregates the received data into a first data set based on the drug identifier value. The computer system optimizes the first pharmacology model using the first data set, thereby generating a second pharmacology model. The computer system provides access to the optimized second pharmacology model.

18 Claims, 7 Drawing Sheets

(56) References Cited

U.S. PATENT DOCUMENTS

| | | | |
|---|---|---|---|
| 2010/0280986 A1* | 11/2010 | Snoeck | G06F 19/3456 |
| | | | 706/54 |
| 2019/0008760 A1* | 1/2019 | Meltzer | A61K 31/56 |
| 2019/0326002 A1* | 10/2019 | Mould | A61B 5/4836 |
| 2019/0362846 A1* | 11/2019 | Vodencarevic | G16H 50/30 |

* cited by examiner

PHARMACOLOGY MODEL OPTIMIZATION BASED ON DISTRIBUTED DATA ACQUISITION

BACKGROUND

Various characteristics of a patient may influence the extent of the patient's response to a medication. Current conventional systems rely on simplified dosing guidelines, and in certain cases, a static pharmacology model. Individualized patient dosing of a medication is essential for a desired therapeutic effect. Patients receiving complex medications benefit from optimal dosing and conventional technology that assists doctors and clinicians in determining the proper dosing for each patient is still limited in effectiveness.

SUMMARY

Described herein is an exemplary system and methods for pharmacology model optimization and deployment based on distributed data acquisition. The system and methods generate an optimized pharmacology model based on acquisition of data from distributed devices where the data generated is associated with dosage recommendation according to the pharmacology model. The pharmacology model provides an output describing the pharmacological effect of the administration of a drug dose over a particular time course. Patient data (which may include pharmacokinetic and/or pharmacodynamic information and/or pharmacological data) is obtained from the distributed devices, scrubbed and aggregated in a manner that may be used to optimize the pharmacology model. An optimized pharmacology model is then distributed or made accessible via an application programming interface (API) to other systems and/or via a user interface provided by the system for interaction and use of the optimized pharmacology model to determine customized, patient-specific medication dosing regimens that indicate medication dosing protocols that include, for example, amount of medication per dose, type of medication, frequency of dosing, etc.

Disclosed embodiments relate to a method and system for a Dosage Customizer that customizes one or more medication dosing regimens for a patient(s). Current conventional systems are limited in how precisely customized a medication dosing regimen can be among different patients being administered the same medication. For example, a patient's genetics, co-administered medication(s), age, sex, race, and biomarkers may be a variable(s) that may require a highly customized dosing regimen. Even more advanced conventional dosing calculator systems do not provide a solution for continuously relearning and optimizing models that predict a customized medication dosing regimen that will most likely result in a therapeutic benefit by separately accounting for each patient's individual characteristics.

In one embodiment, the Dosage Customizer stores a first pharmacology model describing the pharmacokinetics and/or pharmacodynamics for a particular medication. The computer system receives patient data including pharmacological data and data values for a drug identifier and a model identifier. The pharmacological data being associated to drug dosing for the particular medication. The computer system aggregates the received data into a first data set based on the drug identifier value. The computer system executes optimization of the first pharmacology model using the first data set, thereby generating an optimized second pharmacology model. The computer system provides access to the optimized second pharmacology model and allows the calculation of an optimal dosing regimen for a specific patient(s) based on given targets and constraints.

In one embodiment, the Dosage Customizer stores a first pharmacology model that is based on patient data of a plurality of patients with respect to a particular medication(s). The patient data may include, as per each respective patient: dosing administration data, demographics data and lab work data (e.g. medication concentration level(s), serum creatinine level(s) and one or more biomarkers). The Dosage Customizer implements the first pharmacology model to predict a customized dosing regimen for each patient given their personal instances of patient data. The Dosage Customizer may be deployed via a precision dosing platform that continually optimizes and validates the corresponding pharmacology model through one or more non-linear mixed effects (NLME) models and/or continuous machine learning (ML) methods and models. The pharmacology model is optimized according to additional patient data received from existing patients and new patients to whom the particular medication is subsequently administered. A new, subsequent optimized second pharmacology model may be generated by the Dosage Customizer as a refined and updated version of the previous first pharmacology model. The Dosage Customizer may validate the optimized second pharmacology model based on its improvement in precision and accuracy compared to the previous first pharmacology model. In one embodiment, the Dosage Customizer may further identify one or more new covariates as variables for the optimized second pharmacology model.

In one embodiment, the Dosage Customizer may generate and include and perform one or more software modules for operation at a user device. The software modules may include instructions for rendering a Dosage Customizer user interface at a user device(s), collecting and sending patient data and displaying output data from one or more pharmacology models. The software modules may further include instructions for receiving and executing one or more pharmacology models, receiving and executing one or more portions of pharmacology models and accessing pharmacology models stored and executed in a cloud-based Dosage Customizer system. The software modules may further include instructions to receive data provided by an end-user to be included during pharmacology model optimization and execution. For example, an end-user may input, via the Dosage Customizer user interface, one or more variables for an institutional protocol that will be accounted for by the Dosage Customizer during generation of a customized dosing regimen(s).

Some implementations are implemented by a computer system. A computer system can include a processor, a memory, and a non-transitory computer-readable medium. The memory and non-transitory medium can store instructions for performing methods and steps described herein.

Further areas of applicability of the present disclosure will become apparent from the detailed description, the claims and the drawings. The detailed description and specific examples are intended for illustration only and are not intended to limit the scope of the disclosure.

BRIEF DESCRIPTION OF THE DRAWINGS

The present disclosure will become better understood from the detailed description and the drawings, wherein.

DETAILED DESCRIPTION

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

Some embodiments are implemented by a computer system. A computer system may include a processor, a memory, and a non-transitory computer-readable medium. The memory and non-transitory medium may store instructions for performing methods and steps described herein.

Figure 1A:
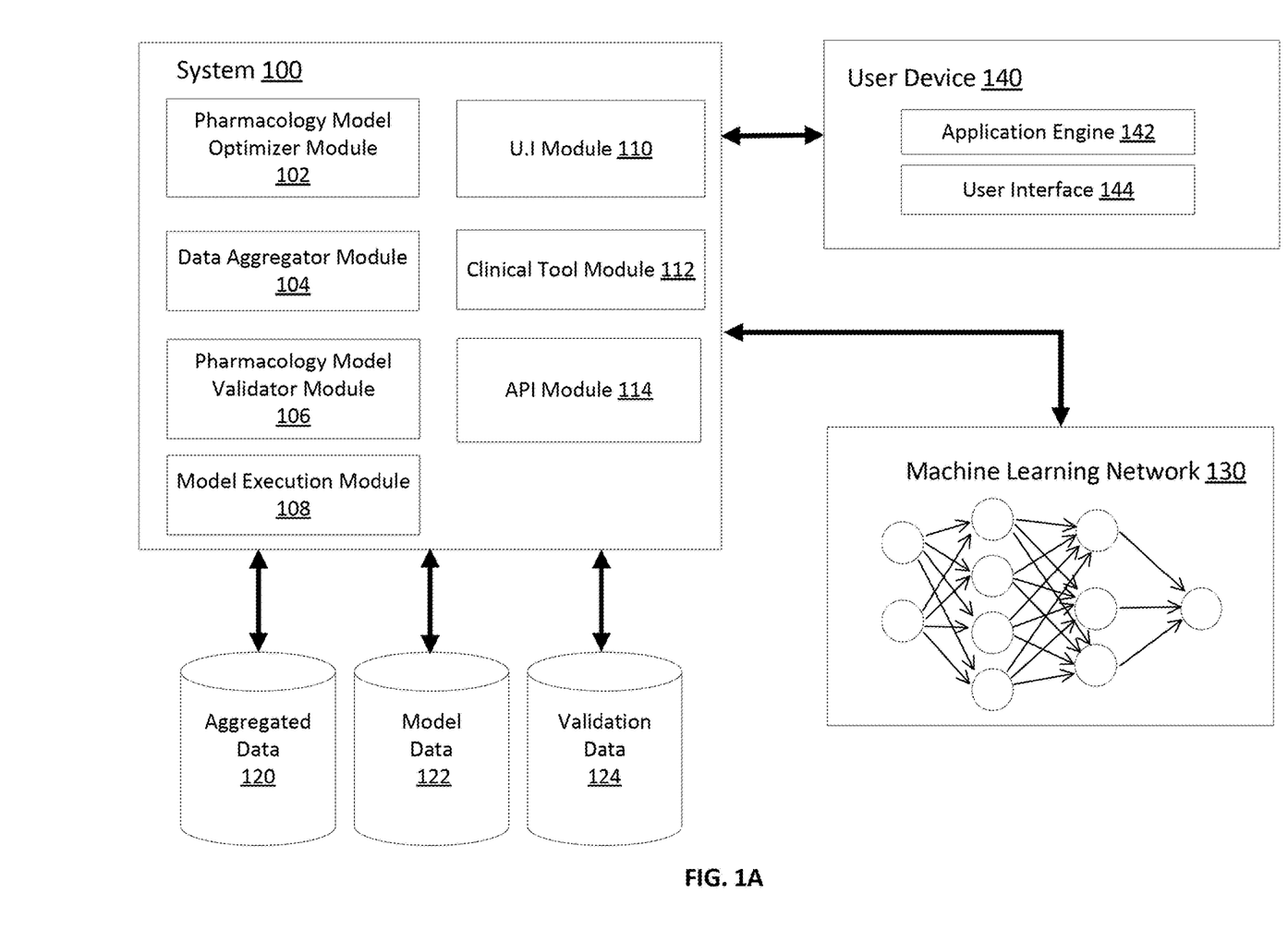
FIG. 1A illustrates an example environment in which embodiments of the invention may operate.

As shown in FIG. 1A, an example system 100 of the Dosage Customizer may include a pharmacology model optimizer module 102, a data aggregator module 104, a pharmacology model validator module 106, model execution module 108, a user interface (U.I.) module 110, a clinical tool module 112 and an API module 114. The system 100 may communicate with a user device 140 to display output, via a user interface 144 generated by an application engine 142. A predictive modeling framework 130 and one or more databases 120, 122, 124 may further be components of the system 100 as well.

The pharmacology model optimizer module 102 of the system 100 may perform functionality as illustrated in FIGS. 1B, 2A-2B and 3.

Figure 2A:
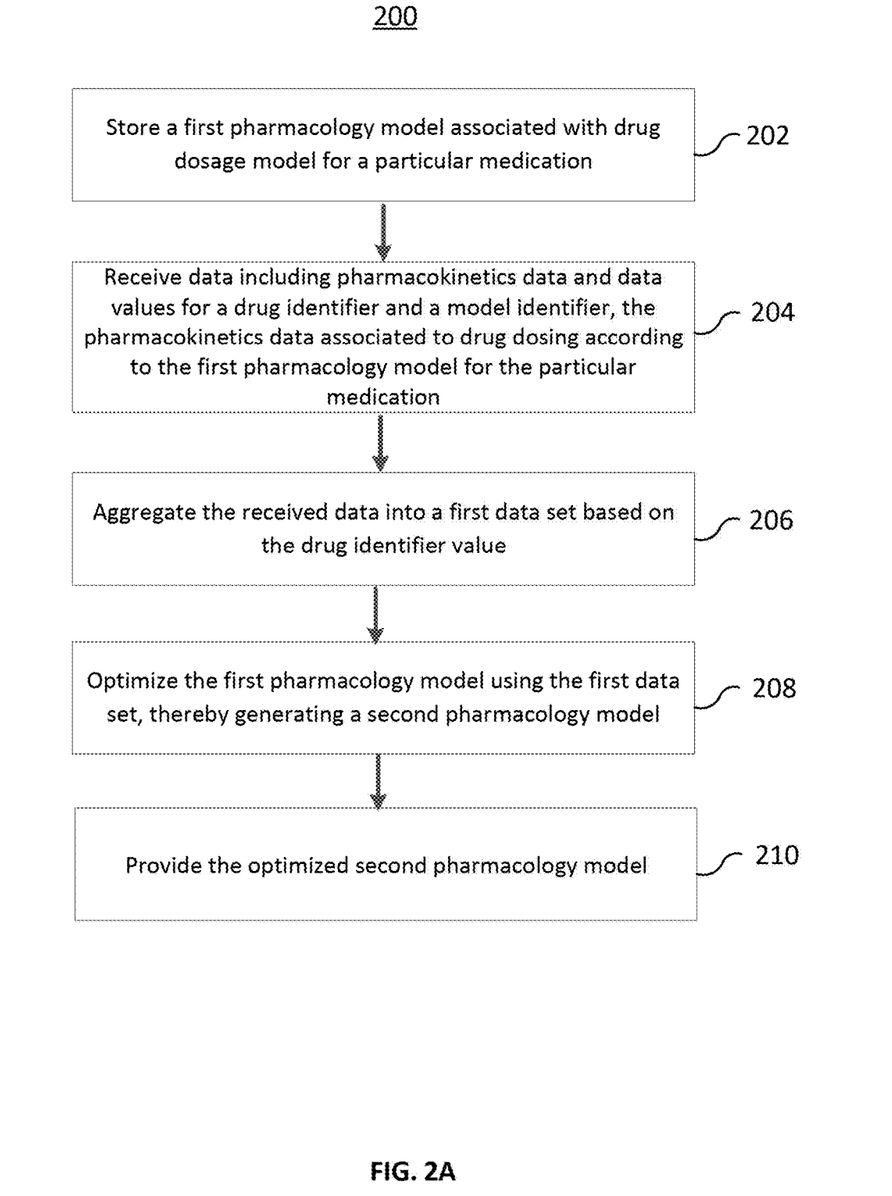
FIGS. 2A-2B illustrate example methods of one or embodiments.
Figure 2B:
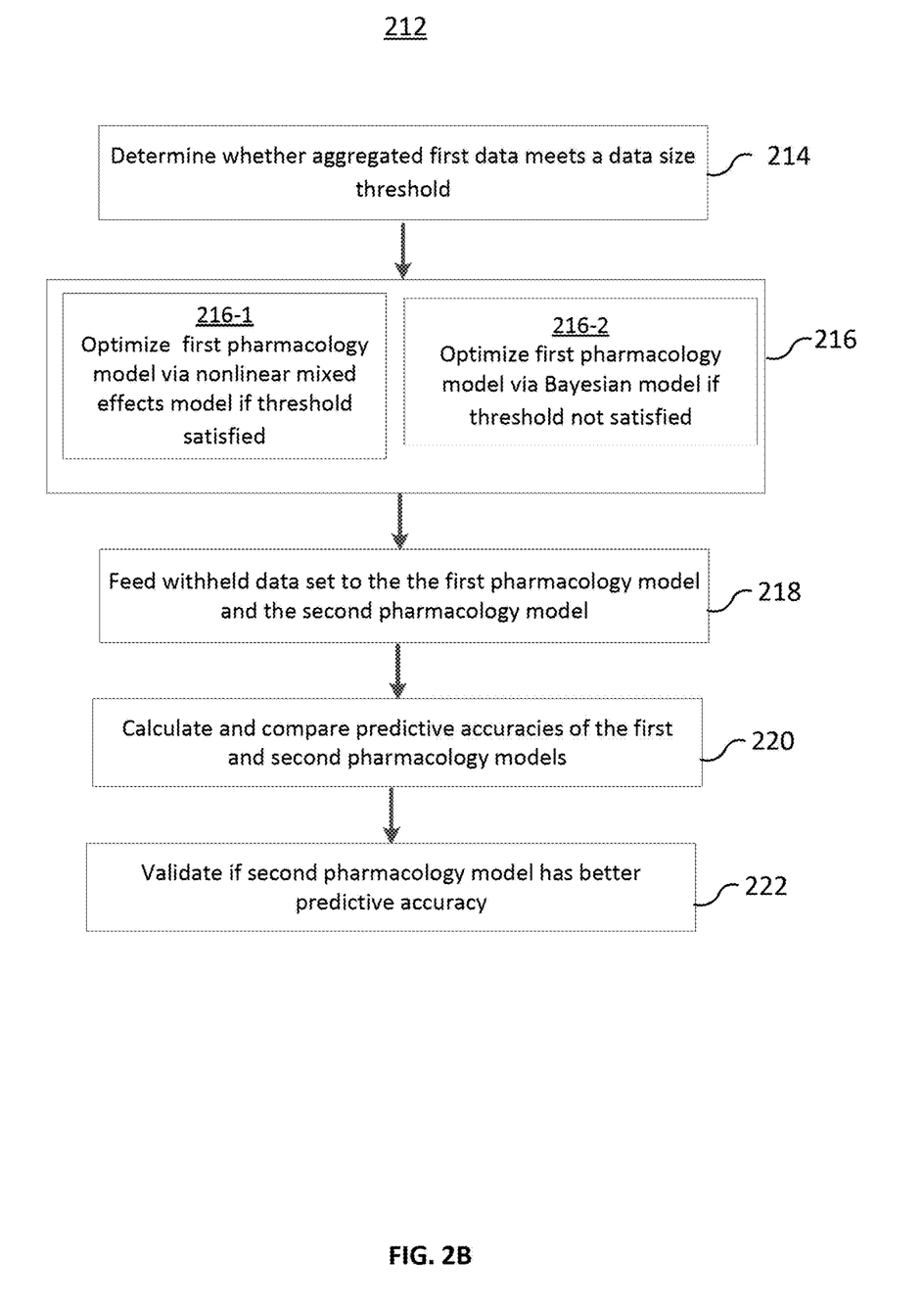

The data aggregator module 104 of the system 100 may perform functionality as illustrated in FIGS. 2A-2B.

The pharmacology model validator module 106 of the system 100 may perform functionality as illustrated in FIGS. 1B, 2A-2B and 3.

Figure 3:
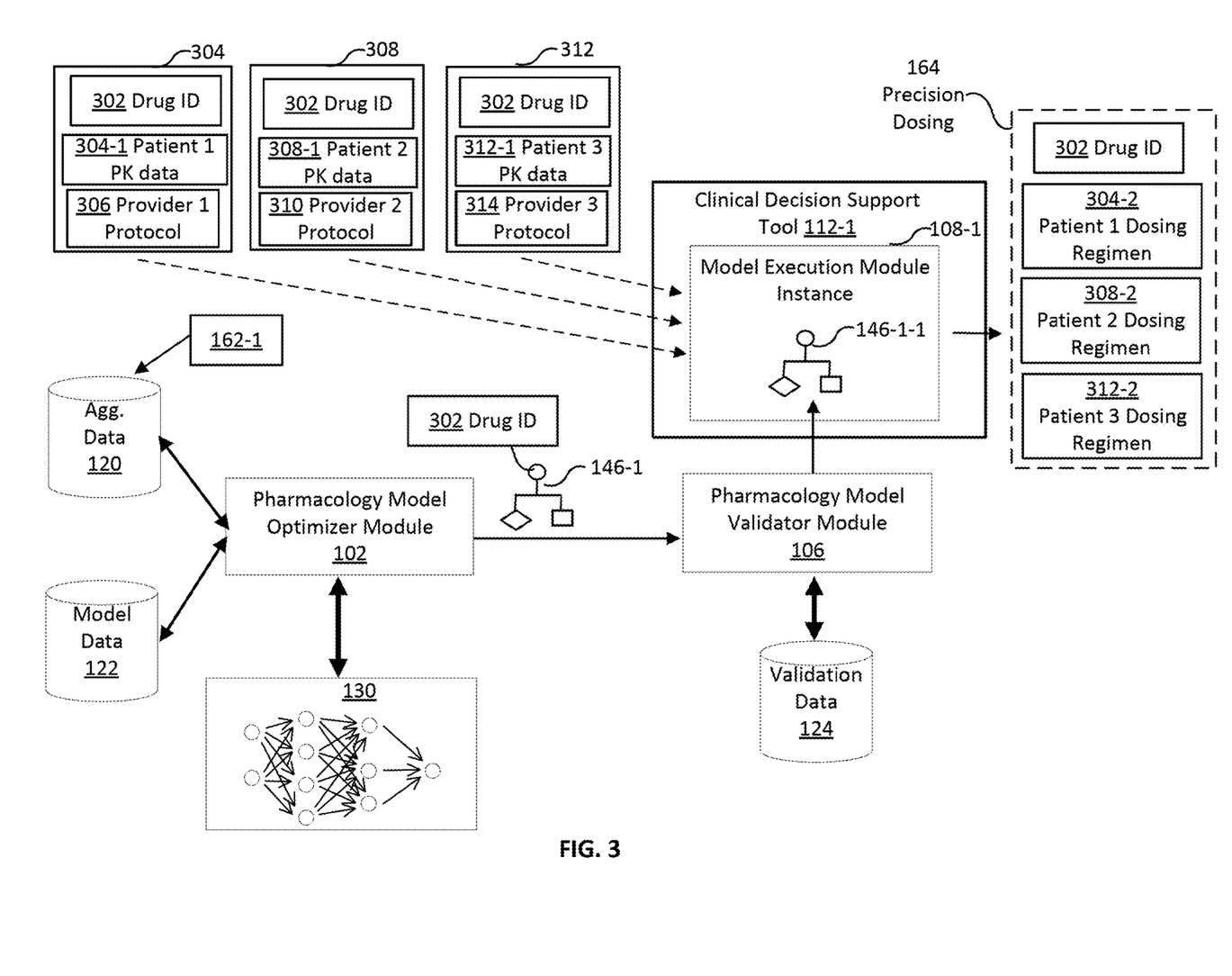
FIG. 3 is an example diagram of one or more embodiments.
Figure 4:
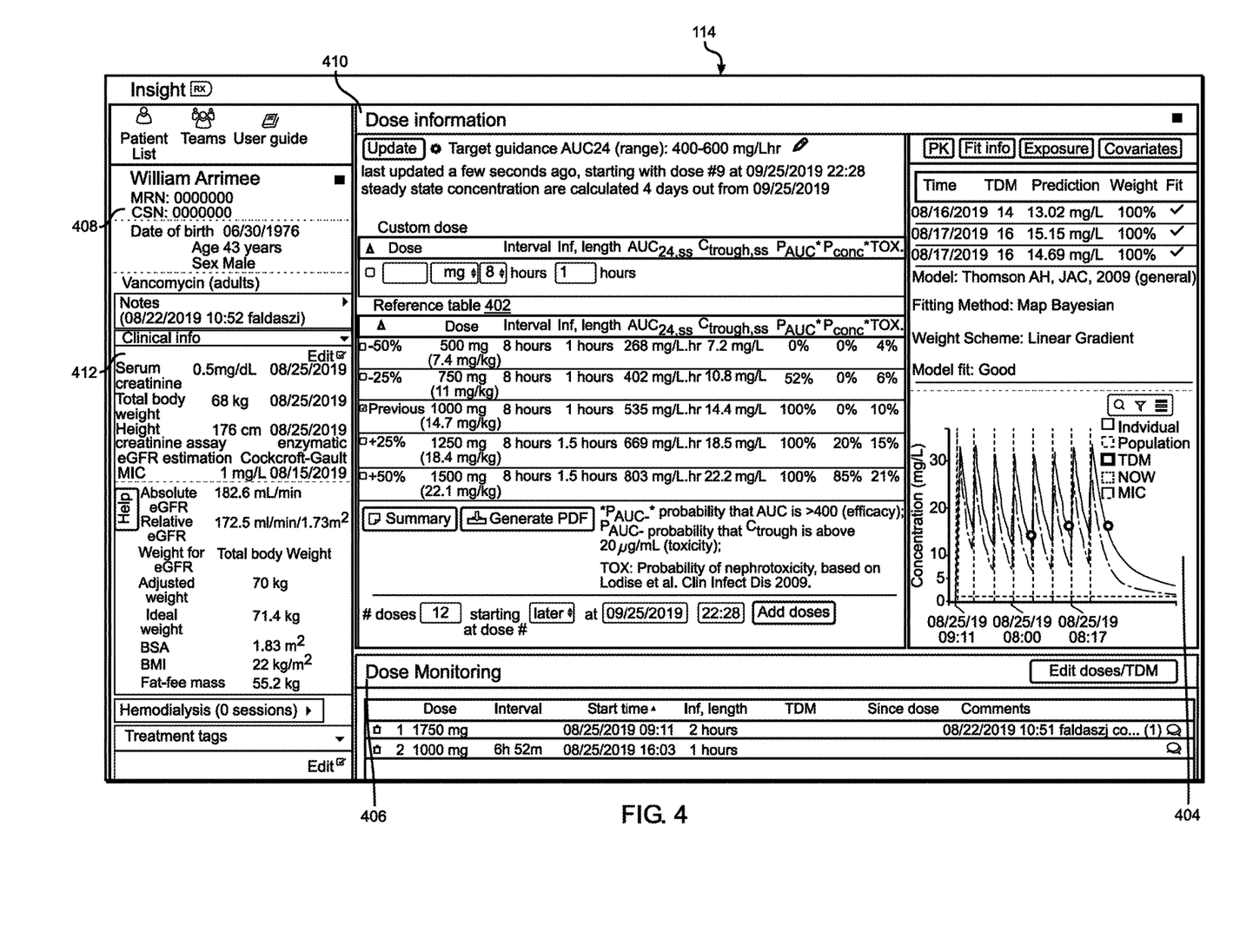
FIG. 4 is an example diagram of a user interface of one or more embodiments.

The model execution module 108 of the system 100 may perform functionality as illustrated in FIGS. 2B, 3 and 4.

The user interface (U.I.) module 110 of the system 100 may perform any functionality with respect to causing display of any output, input, data and information of the system 100 the user interface 144 and as illustrated in FIG. 4.

Figure 1B:
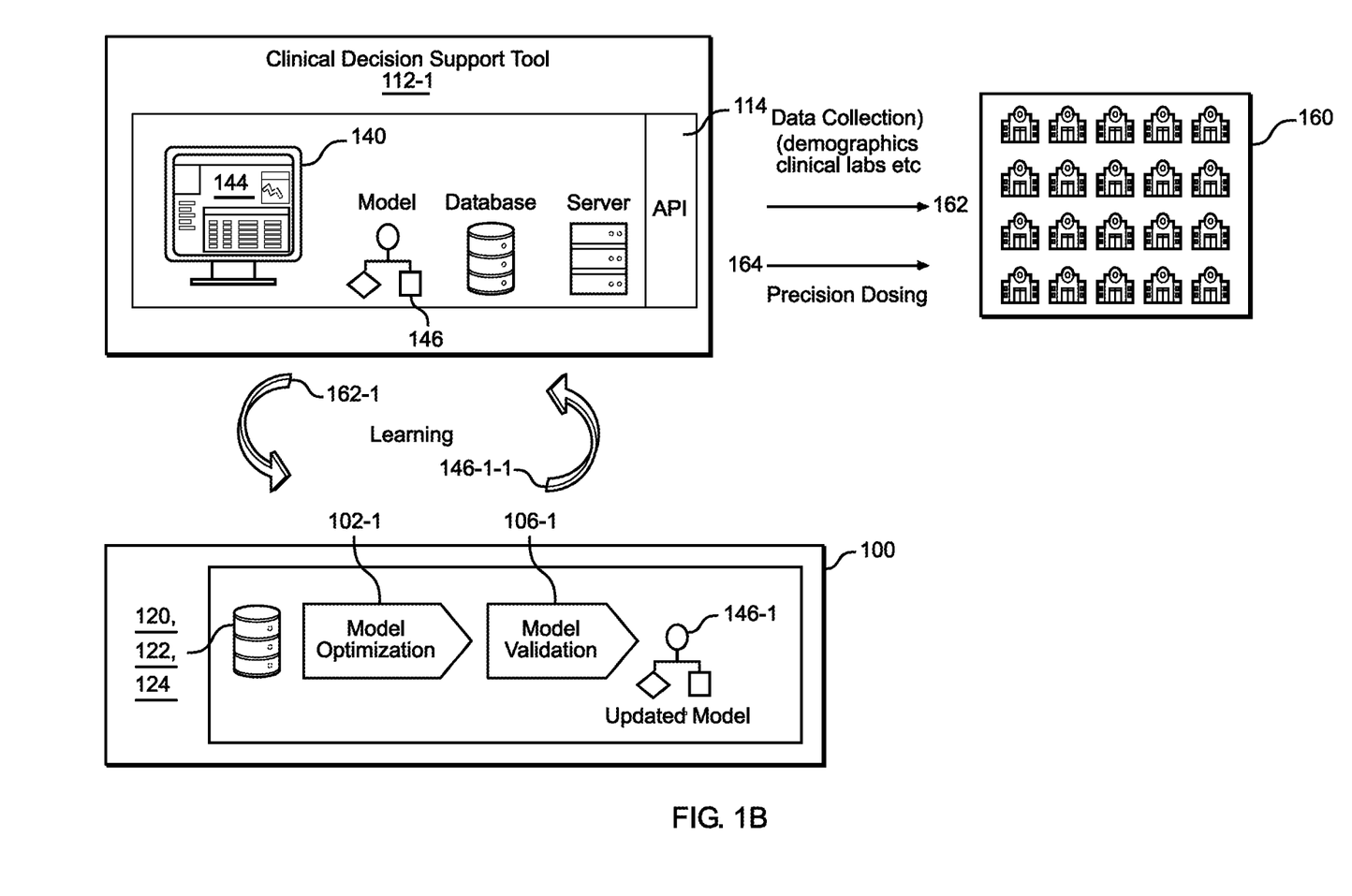
FIG. 1B is an example dataflow diagram and a framework of one or more embodiments.

The clinical tool module 112 of the system 100 may perform functionality as illustrated in FIGS. 1B, 3 and 4.

The API module 114 of the system 100 may perform application programming interface functionality as described herein.

While the databases 120, 122 and 124 are displayed separately, the databases and information maintained in a database may be combined together or further separated in a manner the promotes retrieval and storage efficiency and/or data security.

As shown in FIG. 1B, the Dosage Customizer may be a continuous learning framework that enables optimization of pharmacology models 146, 146-1 with real-world clinical data 162 collected from a plurality of institutional providers 160 (e.g. hospitals). It is understood that various embodiments of the continuous learning framework may include a clinical decision support tool 112-1 of the Dosage Customizer and the system 100 of the Dosage Customizer. The clinical decision support tool 112-1 may include one or more software module(s) accessed via a network and/or downloaded from the clinical tool module 112 and installed at the user device 140. In some embodiments, the clinical decision support tool 112-1 is a module or component of the system 100. The pharmacology models 146, 146-1 may be, for example, one or more pharmacokinetic/pharmacodynamic models. The clinical decision support tool 112-1 may receive the clinical data 162 from the providers 160. The providers 160 may communicate with the clinical decision support tool 112-1 via an application programming interface(s) (API) of the API module 114. For example, the API(s) may be compatible with one or more health information exchange protocols (e.g. Fast Healthcare Interoperability Resources (FHIR), Health Level Seven (HL7), HL7 Clinical Document Architecture (CDA)). The clinical decision support tool 112-1 may have access to local database(s) and local server(s), remote server(s) and/or a cloud computing system. The clinical decision support tool 112-1 may have access to a currently deployed pharmacology model 146 locally. However, it is understood that the currently deployed pharmacology model 146 may be accessed by the clinical decision support tool 112-1 via a cloud-based system associated with the Dosage Customizer. In one embodiment, the clinical decision support tool 112-1 may access the currently deployed pharmacology model 146 stored at a location determined by the system 100.

The clinical decision support tool 112-1 may request, via the pharmacology model execution module 108, execution of a pharmacology model 146 in response, for example, to an end-user selection of a model functionality displayed by user interface 144. In another embodiment, execution of the model 146 may be triggered based on a satisfaction of one more pre-defined criteria independent from end-user activity, such as a pre-defined amount of sample size data. Execution of the current pharmacology model 146 may be based on input patient data that is the most current patient data and may also include a portion(s) of input patient data previously collected. In addition, the user interface 144 may receive additional model input as one or more constraints, protocols, variables and requirements specific to a given provider or a particular patient, or one or more model updates. The input patient data and the additional model input may be fed into the pharmacology model 146 in response to the request from the clinical decision support tool 112-1. For example, the clinical decision support tool 112-1 may include a software module(s) provided by the Dosage Customizer to initiate, monitor and control execution of the pharmacology model 146.

Execution of the currently deployed pharmacology model 146, via the pharmacology model execution module 108, generates optimized dosing regimen 164 (i.e. output data, precision dosing) that describes one or more customized dosing regimens for one or more patients receiving a particular medication at the providers 160 (such as a hospital(s)). For example, a customized dosing regimen for a particular patient of the same, particular medication being administered to one or more patients treated at one or more of the providers 160 will be included in the optimized dosing regimen 164. Each respective patient is thereby associated with a patient-specific, customized dosing regimen(s) in the optimized dosing regimen 164 (i.e. output data, precision dosing) generated by the currently deployed pharmacology model 146. It is understood that the various dosing regimen(s) in the optimized dosing regimen 164 may be calculated to be different in order to produce a similar, predicted therapeutic result across all dosed patients. For example, there may be one or more versions of the currently deployed pharmacology model 146 specific to a particular drug, patient population, and or disease indication. It is understood that, in various embodiments, optimized dosing regimen 164 is deployed on a per-patient basis. That is, a first precision dosing may be output for a first patient and then a second precision dosing may be output for a second patient, where the first precision dosing and the second precision dosing are determined by the model 146 independently.

Additionally, the system 100 may provide an API that allows for integration with separate systems where the separate system may provide required data inputs for an optimized pharmacology model 146. Furthermore, the API will enable authorized third-party companies to access the optimized models from system 100. The pharmacology model execution module 108 may then process the data inputs, and then provide a response to the separate system. For example, the response may be information for precising dosing 164 of a particular drug.

The system 100 of the Dosage Customizer receives clinical support data 162-1 from the clinical decision support tool 112-1. The clinical support data 162-1 may include any patient data received from the providers 160 as well as any portion(s) of the additional model input (e.g. medication administration time, dosing information, patient demographics, clinical labs etc.). The clinical support data 162-1 may further include a drug identifier. The drug identifier may be an alpha-number value that identifies a particular pharmaceutical or medicine. The system 100 may execute a dataflow processed at least by the pharmacology model optimizer module 102 and the pharmacology model validator module 106. The pharmacology model optimizer module 102 performs a model optimization phase 102-1 to execute model optimization in order to generate an updated and optimized version of the pharmacology model 146-1. The pharmacology model validator module 106 performs a model validation phase 106-1. The model validation phase 106-1 compares the precision and accuracy of the currently deployed pharmacology model 146 and the optimized pharmacology model 146-1 and performs sanity checks to evaluate the validity of the model 146-1. If the precision/accuracy of the optimized pharmacology model 146-1 is an improvement on the precision accuracy of the currently deployed pharmacology model 146 and all sanity checks pass, the system 100 deploys an instance 146-1-1 of optimized pharmacology model 146-1 for access and use by the clinical decision support tool 112-1. It is understood that the example dataflow of the system 100, as shown in FIG. 1B, may implicate the use other modules, components and parts of the system 100.

As shown in the example method 200 of FIG. 2A, the system 100 of the Dosage Customizer stores a first pharmacology model associated with a drug dosing model for a particular medication (Act 202). For example, the system 100 may generate a first pharmacology model for a first medication and may further generate other pharmacology models for respective different medications as well. In one embodiment, the system 100 may store the first pharmacology model in relation to a drug identifier that corresponds to the first medication. Each medication has a corresponding unique drug identifier.

The system 100 receives patient data and data values for a drug identifier and a pharmacology model identifier (Act 204). The pharmacology model identifier may be an alphanumeric value associated with a particular pharmacology model that was used during the assessment of the patient data (which includes pharmacokinetic data and dose determination). For example, the system 100 may receive patient data that was associated by two different pharmacology models for the same drug identifier. The system 100 may segment the data into respective data sets based on the drug identifier as well as other downstream attributes such as indication and disease subtype. The system 100 may then execute optimization of the particular pharmacology model based on received patient data and the different associated pharmacology models used for the same drug (e.g., using the same drug identifier). In various embodiments, execution of optimization of the model 146 will occur for a drug that has a single type of model. It is understood that a first drug may be associated with a model version (or model type) that is different than a model version (or model type) for a second drug. It is further understood that model optimization is executed with respect to drugs with one or more biomarkers.

Patient data may be associated to drug dosing determined according to a previously (or currently) deployed first pharmacology model(s) for the particular medication. The particular medication corresponds to the unique received drug identifier. The patient data may include at least one of: pharmacokinetic data, dosing administration data, patient demographic data and patient laboratory data. It is understood that one or more portions of the patient data may be used during execution of a pharmacology model(s) in order to determine dosing output (such as precision dosing). One or more data sets may be separate according to drug (medication) type and model type. The dosing administration data represents a dose(s) of the particular medication received by the respective patient and any dose(s) of one or more co-administered medications received by the respective patient. Patient demographic data may describe a patient's age, body weight and sex. The patient laboratory data may provide values for one or more drug concentration levels in the respective patient, one or more serum creatinine levels of the respective patient and one or more drug-related biomarkers of the respective patient.

The system 100 aggregates the received data (dosing administration data, patient demographic, patient laboratory data, etc.), into a first optimization data set based on the drug identifier value (Act 206). The data aggregator module 104 identifies the first optimization data set which includes previous data associated with the received drug identifier value. The previous data may be pharmacokinetics data received prior to the most recently received pharmacokinetics data. The previous data may have been used to optimize a currently deployed pharmacology model. The data aggregator module 104 may insert the received data into the first optimization data set. The data aggregator module 104 may perform an error check on the aggregated data to determine whether a value(s) for a certain data variable(s) in the received data is missing whereas a previous value exists in the previous data. The error checking may further include reconciling different formats of the received data and the previous data. For example, the data aggregator module 104 may detect the received data is structured differently than the previous data. The data aggregator module 104 may resolve the differences between the structures of the received and previous data in order to identify which values in the received data are associated with the same data type (i.e. data record field) of values in the previous data.

Additionally, the data aggregator module 104 may also identify the occurrence of any particular patient identifying data that may be included in the received data. The data aggregator module 104 may remove (i.e. scrub) the patient identifying data so that the aggregated data set only use anonymized information. For example, the data aggregator module 104 may search received data to determine if any of the received data includes information that uniquely identifies a patient (such as name, social security number, patient ID number, patient record number, etc.). The data aggregator module 104 would then delete the patient identifying data from the received data, and then store the received data in anonymized form. The original received data may then be deleted and wiped from any system 100 storage device.

The system 100 optimizes the first pharmacology model using the first optimization data set, thereby generating an optimized second pharmacology model (Act 208). The optimized second pharmacology model is an updated, refined and more predictive version of the first pharmacology model. The pharmacology model optimizer module 102 may optimize the first pharmacology model by feeding the first optimization data set into various types of drug dosage models, such as, for example, machine learning models and/or non-linear effects models available in the predictive modeling framework 130. The system 100 may use any suitable machine learning training technique to train the machine learning network 130, including, but not limited to a Non-Linear Mixed Effects (NLME) models, e.g. implemented using gradient-based methods (e.g. first-order conditional estimation, FOCE), or using sampling-based methods such as Markov-Chain Monte Carlo (MCMC) or Stochastic Approximation Expectation maximization (SAEM); or a neural net based algorithm, such as Artificial Neural Network, Deep Learning; a robust linear regression algorithm, such as Random Sample Consensus, Huber Regression, or Theil-Sen Estimator; a kernel based approach like a Support Vector Machine and Kernel Ridge Regression; a tree-based algorithm, such as Classification and Regression Tree, Random Forest, Extra Tree, Gradient Boost Machine, or Alternating Model Tree; Naïve Bayes Classifier; and others suitable machine learning algorithms.

The system 100 provides the optimized second pharmacology model (Act 210). The optimized second pharmacology model may be executed on patient data (which includes pharmacokinetic data) to generate output data. For example, the system 100 provides the optimized second pharmacology model for performing one or more pharmacokinetic simulations on patient-specific data to generate output data. The generated output data includes pharmacology simulations of one or more customized patient dosing regimens of the particular medication. In one embodiment, the output data consists of pharmacokinetic simulations for different dosing regimens as well as patient-specific exposure metrics calculated from the pharmacokinetic simulations. The simulations are generated using a drug-specific pharmacology model (e.g. first or updated/optimized pharmacology model), data for the specific patient, and, for example, Bayesian algorithms.

As shown in the example method 212 of FIG. 2B, to optimize the first pharmacology model, the system 100 may determine whether the aggregated data (or first optimization data set) meets a data size threshold (Act 214). For example, the system 100 may aggregate received data from multiple sources, such as a web-based interface and/or from separate remote electronic health record systems. The received data is stored and collected in a database 120 until a threshold number of records associated with a drug identifier is collected. The threshold number of records (i.e., a data size threshold) allows the system 100 to set a predetermined threshold sample. The system 100 may monitor that a threshold number of electronic data records for the drug identifier has been received, and then automatically initiate the model optimization process as described herein. Moreover, the system 100 may monitor and track data size thresholds for multiple drug identifiers. For example, the system 100 may set different data size optimization trigger thresholds for different drug identifiers. A data size threshold for a first drug identifier may, for example, be set at 1000 records or samples, while a data size threshold for a second drug identifier may, for example, be set at 1200 records or samples.

While the system 100 may reach the predetermined data size threshold to trigger execution of the optimization process described herein, the system 100 may continue to receive and aggregate additional data records associated the particular drug or particular pharmacology model. In this situation, the system 100 may set a secondary, tertiary, and so forth, data size threshold to aggregate the additional received data. For example, the system 100 may set a secondary data size threshold (such as 500 records or samples), where upon meeting this threshold the system 100 will aggregate the newly received data for the secondary data size threshold with the initial aggregated data for the original data threshold data. The system 100 may aggregate both sets of data into data set and used the data set re-optimize the same pharmacology model that was optimized using the first aggregated data set. Continued aggregation of received data associated with a particular pharmacology model allows the system 100 to periodically, subsequently re-optimize a specific pharmacology model when a predetermined number of records or samples have been received.

The pharmacology model optimizer module 102 may use nonlinear mixed effects modeling or other modeling methods for optimizing the first pharmacology model based on the whether or not the data size threshold is satisfied (Act 216). If the data size threshold is satisfied, the pharmacology model optimizer module 102 may feed the first optimization data set (or the aggregated data) into a nonlinear mixed effects model to generate the second pharmacology model (Act 216-1). If the data size threshold is not satisfied, the pharmacology model optimizer module 102 may feed the first optimization data set into a Bayesian model to generate the second pharmacology model (Act 216-2). It is understood that various other predictive models may be employed to generate the optimized second pharmacology model. In one embodiment, the pharmacology model optimizer module 102 may test for covariates according to a generalized additive model approach or a stepwise covariate modeling approach.

The pharmacology model validator module 106 may validate the optimized second pharmacology model before it is deployed. The optimized second pharmacology model may be compared to the first pharmacology model by assessing various diagnostic metrics of predictive accuracy to assess the precision and bias of the second pharmacology model on a withheld data set. The pharmacology model validator module 106 may feed the withheld data set into both the first pharmacology model and the optimized second pharmacology model in order to validate if optimizing the first pharmacology model with, for example, the recent received data resulted in a more precise second pharmacology model (Act 218). For example, the withheld data set may be data that has not been used to generate any pharmacology model(s) such that its values have not been used to identify covariates, features and bias.

The output from executing the first and optimized second pharmacology models on the withheld data set is used by the pharmacology model validator module 106 to calculate predictive accuracy values for both pharmacology models (Act 220). In one embodiment, the predictive accuracy as between the first and second pharmacology models may be assessed using a root mean squared error approach and/or a mean absolute percentage error approach or other measures of predictive precision and bias. If the pharmacology model validator module 106 determines the optimized second pharmacology model has a better predictive accuracy than the first pharmacology model, the optimized second pharmacology model is thereby validated and deployed in place of or in addition to the first pharmacology model (Act 222).

As shown in FIG. 3, the pharmacology model optimizer module 102 accesses aggregated data 120 and model data 122 in order to optimize a currently deployed first pharmacology model for generating precision dosing 164 of a particular medication that corresponds with a drug identifier 302. The model data 122 may include data related to one or more features, covariates, variables, coefficients and coefficient weights of one or more models in the predictive modeling framework 130 that may be implemented to optimize the first pharmacology model. The model data 122 may also include one or more drug dosage models based one or more machine learning training techniques. The pharmacology model optimizer module 102 may identify one or more predictive models in the predictive modeling framework 130 stored in relation to the drug identifier 302. The pharmacology model optimizer module 102 may optimize the first pharmacology model according to an identified model(s) over the aggregated data 120 and model data 122 to generate an optimized pharmacology model 146-1 associated with the drug identifier 302. It is understood that in various embodiments, the predictive modeling framework 130 includes one more types of nonlinear mixed effects models and one or more types of machine leaning models.

The system 100 may assign a unique model identifier for each of the optimized pharmacology models. For example, different optimized models may be generated by the system 100 based on the evaluation of the aggregated data. The model identifier may then be used by the system 100 to track a particular instance of the pharmacology model used by the model execution module 108. As discussed previously, the system 100 may segment or aggregate data based on the particular pharmacology model (e.g., using the model identifier) that was used to generate the received data.

The pharmacology model validator module 106 may receive the optimized pharmacology model 146-1 and accesses validation data 124 to identify a withheld data set. The pharmacology model validator module 106 may execute the first pharmacology model and the optimized pharmacology model 146-1 over the withheld data set to determine which of the two models have a better predictive accuracy. Upon determining the optimized pharmacology model 146-1 has a better predictive accuracy, the pharmacology model validator module 106 may provide the optimized and validated pharmacology model 146-1-1 to a clinical decision support tool 112-1.

The clinical decision support tool 112-1 may have an installed instance of the model execution module 108-1 provided by the model execution module 108 and operation in conjunction with a user device 140 to receive data input for execution of an optimized pharmacology model. The clinical decision support tool 112-1 may receive patient health data 304, 308, 312 associated with many, different patients, such as for example, three different patients, where each patient is being treated at different providers (e.g. hospitals). Each patient health data 304, 308, 312 may include the drug identifier 302, the respective patient's biomarker data included in the data 304-1, 308-1, 312-1 for determining precision dosing (i.e. dosing output) 164 and additional data related to the specific provider 306, 310, 314, such as provider-specific protocols for administering the particular medication.

The model execution module 108-1 may execute the optimized pharmacology model 146-1 on each of the received receive patient health data 304, 308, 312. The model execution module 108-1 generates dosing output data that includes precision dosing (such as, for example, an individualized dosing regimen) 164. The precision dosing output 164 may be generated on a per-patient basis and include a customized dosing regimen 304-2, 308-2, 312-2 for each respective patient that accounts for the patient's characteristics, clinical requirements and constraints 304-1, 308-1, 312-1 provided in patient data and the additional data related to the specific model 306, 310, 314. Each customized dosing regimen 304-2, 308-2, 312-2 may thereby be different for each patient in terms of, for example, the dose amount(s), dose frequency, dosing time(s) of day and scheduled laboratory data collection. Although the customized dosing regimens 304-2, 308-2, 312-2 may be different, such differences for each patient is predicted by the optimized pharmacology model 146-1 to most likely result in the highest/most optimal therapeutic effect (or efficacy) of the particular medication. It is understood that the precision dosing output 164 may provide the customized dosing regimens 304-2, 308-2, 312-2 for each respective patient sequentially (one at a time) such that determination of the dosing regimens 304-2, 308-2, 312-2 are made independently of each other. In various embodiments, the model 146 (or any optimized model instance 146-1) may have predefined input variables necessary to be optimized and executed. In addition, additional, exploratory data from one or more providers may also be received and aggregated to be included in model optimization.

An example of a user interface 144 for the Dosage Customizer is shown in FIG. 4. The user interface 144 is displayed at a user device 140. For example, the user device 140 may be part of a clinical decision support tool 112-1 of the Dosage Customizer. The user interface 144 may include a reference table 402, a visualization panel 404, a drug monitoring panel 406, a patient panel 408, a custom dose menu 410 and a clinical panel 412

The reference table 402 may provide interactive functionality to allow an end-user to access, assess and adjust various types of data, such as a patient's customized dosing regimen. The reference table 402 may further allow the end-user to review a patient's pharmacology metrics, such as Ctrough, Cmax and AUC. The reference table 402 may allow the end-user to add notation for transmission to and insertion into a patient's electronic health record.

The visualization panel 404 may provide interactive functionality to allow an end-user to access and view a patient's patient data and run patient-specific model simulations on various dosing regimens. The visualization panel 404 may provide one or more visualizations of concentration-versus-time plots based on the results of the simulations selected by the end-user. The one or more visualizations resulting from the simulations may assist the end-user in identifying, validating and selecting a dosing regimen which is best to use for a given patient that is being administered the particular medication.

The drug monitoring panel 406 may provide interactive functionality to allow an end-user to access, review and edit patient dosing history and therapeutic drug monitoring (TDM) information. Clinical notes may also be entered via the drug monitoring panel 406. The patient panel describes patient information. The user interface may also provide interactive functionality to allow an end-user to access, review and share information with respect to a defined group of end-users. In some embodiments, one or more portions of data from electronic health records may be pulled automatically by the Dosage Optimizer in order to obtain patient data.

The custom dose menu 410 may provide interactive functionality to allow an end-user to further tailor a patient's customized dosing regimen. The clinical panel 412 may provide interactive functionality to allow an end-user to review a patient's clinical characteristics. The clinical panel 412 may allow the end-user to input time-varying clinical characteristics of a patient (e.g. serum creatinine) and select assay types and eGFR estimation methods.

Figure 5:
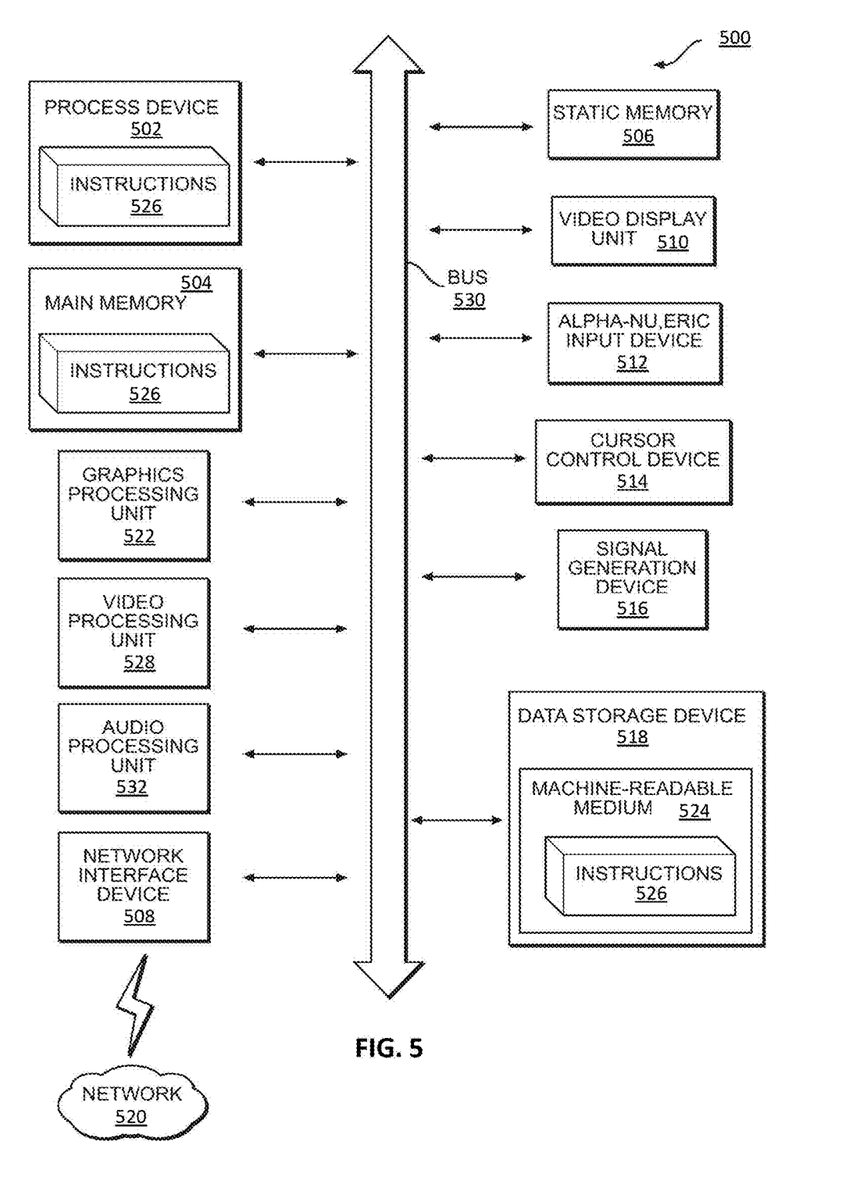
FIG. 5 is an example diagram of one environment in which some embodiments may operate.

FIG. 5 illustrates an example machine of a computer system within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 500 includes a processing device 502, a main memory 504 (e.g., read-only memory (ROM), flash memory, dynamic random access memory (DRAM) such as synchronous DRAM (SDRAM) or Rambus DRAM (RDRAM), etc.), a static memory 506 (e.g., flash memory, static random access memory (SRAM), etc.), and a data storage device 518, which communicate with each other via a bus 530.

Processing device 530 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 502 may also be one or more special-purpose processing devices such as an application specific integrated circuit (ASIC), a field programmable gate array (FPGA), a digital signal processor (DSP), network processor, or the like. The processing device 502 is configured to execute instructions 526 for performing the operations and steps discussed herein.

The computer system 500 may further include a network interface device 508 to communicate over the network 520. The computer system 500 also may include a video display unit 510 (e.g., a liquid crystal display (LCD) or a cathode ray tube (CRT)), an alphanumeric input device 512 (e.g., a keyboard), a cursor control device 514 (e.g., a mouse) or an input touch device, a graphics processing unit 522, a signal generation device 516 (e.g., a speaker), graphics processing unit 522, video processing unit 528, and audio processing unit 532.

The data storage device 518 may include a machine-readable storage medium 524 (also known as a computer-readable medium) on which is stored one or more sets of instructions or software 526 embodying any one or more of the methodologies or functions described herein. The instructions 526 may also reside, completely or at least partially, within the main memory 504 and/or within the processing device 502 during execution thereof by the computer system 500, the main memory 504 and the processing device 502 also constituting machine-readable storage media.

In one implementation, the instructions 526 include instructions to implement functionality corresponding to the components of a device to perform the disclosure herein. While the machine-readable storage medium 524 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

In general, the terms "engine" and "module", as used herein, refer to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on one or more computer readable media, such as compact discs, digital video discs, flash drives, or any other tangible media. Such software code may be stored, partially or fully, on a memory device of the executing computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Various general purpose systems may be used with programs in accordance with the teachings herein, or it may prove convenient to construct a more specialized apparatus to perform the method. The structure for a variety of these systems will appear as set forth in the description above. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A system comprising one or more processors, and a non-transitory computer-readable medium including one or more sequences of instructions that, when executed by the one or more processors, cause the system to perform operations comprising:

storing, by a first device, a first pharmacology model associated with a drug dosage model for a particular medication;

receiving, from one or more devices separate from the first device, patient data including pharmacological data and data values for a drug identifier and a pharmacology model identifier, the pharmacological data associated to drug dosing for the particular medication;

aggregating the received data into a first data set based on the drug identifier value, the first data set comprising, in part: one or more drug concentration levels in the respective patient, one or more serum creatinine levels of the respective patient and one or more drug-related biomarkers of the respective patient;

generating a second pharmacology model by optimizing the first pharmacology model via feeding the first data set and the first pharmacology model into a predictive modeling framework, which includes:

(i) feeding first input comprising at least a portion of the first data set and the first pharmacology model into the predictive modeling framework;

(ii) building at least one Non-Linear Mixed Effects (NLME) candidate model, represented by one or more first data structures, based on the first input, wherein the at least one NLME candidate model generates one or more customized patient dosing regimens of the particular medication according to an NLME statistical model resulting from an execution of the at least one NLME statistical model by the one or more separate devices;

(iii) feeding second input comprising at least a different portion of the first data set and the first pharmacology model into the predictive modeling framework;

(iv) building at least one machine learning (ML) candidate model, represented by one or more second data structures, based on the second input, wherein the at least one ML candidate model generates one or more customized patient dosing regimens of the particular medication according to one or more different types of machine learning models resulting from an execution of the at least one ML candidate model by the one or more separate devices; and (v) selecting the optimized second pharmacology model from one of: the at least one NLME candidate model and the at least one ML candidate model;

transmitting the optimized second pharmacology model to the one or more separate devices; and generating user interface data for a visualization panel portion displayable at the one or more separate devices, wherein rendered user interface data for the visualization panel portion at the one or more separate devices portrays one or more visualizations of respective medication concentration-versus-time plots resulting from one or more corresponding simulations of the optimized second pharmacology with respect to the patient-specific data and the one or more customized patient dosing regimens of the particular medication.

2. The system as in claim 1, wherein the patient data further comprises at least one of: pharmacokinetic data, dosing administration data, patient demographic data and patient laboratory data.

3. The system as in claim 2, wherein the patient data is associated with a plurality of patients receiving the drug dosage of the particular medication; and for each respective patient:
(i) the dosing administration data represents: at least one dose of the particular medication received by the respective patient and any dose of one or more co-administered medications received by the respective patient;
(ii) the patient demographic data comprises at least one of: a patient age, a patient body weight and a patient sex.

4. The system as in claim 2, wherein aggregating the received data into a first data set based on the drug identifier value comprises:

wherein the drug identifier in the received data corresponds to the particular medication;
wherein the drug identifier value for the first data set corresponds to the particular medication, the first data set at least comprises previous patient data associated with a dosing of the particular medication.

5. The system as in claim 4, wherein the drug identifier value is associated with one or more pharmacology models and respective portions of patient data.

6. The system as in claim 1, wherein optimizing the first pharmacology model using the first data set, thereby generating a second pharmacology model comprises:

determining whether the aggregated first data set meets a data set size threshold: upon determining the data size threshold is met, optimizing the first pharmacology model by feeding at least a portion of the first data set and one or more existing pharmacology models to build a nonlinear mixed effects model to generate the second pharmacology model; and
validating the generated second pharmacology model.

7. The system as in claim 6, wherein validating the generated second pharmacology model comprises:

feeding a second data set withheld during optimization of the first pharmacology model into the first pharmacology model and into the generated second pharmacology model;
calculating a first predictive accuracy based on output from feeding the second data set into the first pharmacology model;
calculating a second predictive accuracy based on output from feeding the second data set into the generated second pharmacology model; and
validating the generated second pharmacology model upon determining the second predictive accuracy is better than the first predictive accuracy.

8. The system as in claim 1, wherein providing the optimized second pharmacology model for performing on or more pharmacology simulations comprises:

providing the optimized second pharmacology model for performing the one or more pharmacokinetic simulations on the patient-specific data according to one or more dosing regimens.

9. A non-transitory computer-readable medium comprising instructions for:

storing, by a first device, a first pharmacology model associated with a drug dosage model for a particular medication;
receiving, from one or more devices separate from the first device, patient data including pharmacological data and data values for a drug identifier and a pharmacology model identifier, the pharmacological data associated to drug dosing for the particular medication;
aggregating the received data into a first data set based on the drug identifier value, the first data set comprising, in part: one or more drug concentration levels in the respective patient, one or more serum creatinine levels of the respective patient and one or more drug-related biomarkers of the respective patient;
generating a second pharmacology model by optimizing the first pharmacology model via feeding the first data set and the first pharmacology model into a predictive modeling framework, which includes:
(i) feeding first input comprising at least a portion of the first data set and the first pharmacology model into the predictive modeling framework;
(ii) building at least one Non-Linear Mixed Effects (NLME) candidate model, represented by one or more first data structures, based on the first input, wherein the at least one NLME candidate model generates one or more customized patient dosing regimens of the particular medication according to an NLME statistical model resulting from an execution of the at least one NLME statistical model by the one or more separate devices;
(iii) feeding second input comprising at least a different portion of the first data set and the first pharmacology model into the predictive modeling framework;
(iv) building at least one machine learning (ML) candidate model, represented by one or more second data structures, based on the second input, wherein the at least one ML candidate model generates one or more customized patient dosing regimens of the particular medication according to one or more different types of machine learning models resulting from an execution of the at least one ML candidate model by the one or more separate devices; and
(v) selecting the optimized second pharmacology model from one of: the at least one NLME candidate model and the at least one ML candidate model;
transmitting the optimized second pharmacology model to the one or more separate devices; and
generating user interface data for a visualization panel portion displayable at the one or more separate devices, wherein rendered user interface data for the visualization panel portion at the one or more separate devices portrays one or more visualizations of respective medication concentration-versus-time plots resulting from one or more corresponding simulations of the optimized second pharmacology with respect to the patient-specific data and the one or more customized patient dosing regimens of the particular medication.

10. The non-transitory computer-readable medium as in claim 9, wherein the patient data further comprises at least one of: pharmacokinetic data, dosing administration data, patient demographic data and patient laboratory data.

11. The non-transitory computer-readable medium as in claim 10, wherein the patient data is associated with a plurality of patients receiving the drug dosage of the particular medication; and
for each respective patient:
(i) the dosing administration data represents: at least one dose of the particular medication received by the respective patient and any dose of one or more co-administered medications received by the respective patient; and
(ii) the patient demographic data comprises at least one of: a patient age, a patient body weight and a patient sex.

12. The non-transitory computer-readable medium as in claim 9, wherein aggregating the received data into a first data set based on the drug identifier value comprises:
wherein the drug identifier in the received data corresponds to the particular medication;
wherein the drug identifier value for the first data set corresponds to the particular medication, the first data set at least comprises previous patient data associated with a dosing of the particular medication.

13. The non-transitory computer-readable medium as in claim 12, wherein the drug identifier value is associated with one or more pharmacology models and respective portions of patient data.

14. The non-transitory computer-readable medium as in claim 9, wherein optimizing the first pharmacology model using the first data set, thereby generating a second pharmacology model comprises:
determining whether the aggregated first data set meets a data set size threshold: upon determining the data size threshold is met, optimizing the first pharmacology model by feeding at least a portion of the first data set and one or more existing pharmacology models to build a nonlinear mixed effects model to generate the second pharmacology model; and
validating the generated second pharmacology model.

15. The non-transitory computer-readable medium as in claim 14, wherein validating the generated second pharmacology model comprises:
feeding a second data set withheld during optimization of the first pharmacology model into the first pharmacology model and into the generated second pharmacology model;
calculating a first predictive accuracy based on output from feeding the second data set into the first pharmacology model;
calculating a second predictive accuracy based on output from feeding the second data set into the generated second pharmacology model; and
validating the generated second pharmacology model upon determining the second predictive accuracy is better than the first predictive accuracy.

16. The non-transitory computer-readable medium as in claim 9, wherein providing the optimized second pharmacology model for performing on or more pharmacology simulations comprises:
providing the optimized second pharmacology model for performing the one or more pharmacokinetic simulations on the patient-specific data according to one or more dosing regimens.

17. A computer-implemented method comprising:
storing, by a first device, a first pharmacology model associated with a drug dosage model for a particular medication;
receiving, from one or more devices separate from the first device, patient data including pharmacological data and data values for a drug identifier and a pharmacology model identifier, the pharmacological data associated to drug dosing for the particular medication;
aggregating the received data into a first data set based on the drug identifier value, the first data set comprising, in part: one or more drug concentration levels in the respective patient, one or more serum creatinine levels of the respective patient and one or more drug-related biomarkers of the respective patient;
generating a second pharmacology model by optimizing the first pharmacology model via feeding the first data set and the first pharmacology model into a predictive modeling framework, which includes:
(i) feeding first input comprising at least a portion of the first data set and the first pharmacology model into the predictive modeling framework;
(ii) building at least one Non-Linear Mixed Effects (NLME) candidate model, represented by one or more first data structures, based on the first input, wherein the at least one NLME candidate model generates one or more customized patient dosing regimens of the particular medication according to an NLME statistical model resulting from an execution of the at least one NLME statistical model by the one or more separate devices;
(iii) feeding second input comprising at least a different portion of the first data set and the first pharmacology model into the predictive modeling framework;
(iv) building at least one machine learning (ML) candidate model, represented by one or more second data structures, based on the second input, wherein the at least one ML candidate model generates one or more customized patient dosing regimens of the particular medication according to one or more different types of machine learning models resulting from an execution of the at least one ML candidate model by the one or more separate devices; and
(v) selecting the optimized second pharmacology model from one of: the at least one NLME candidate model and the at least one ML candidate model;
transmitting the optimized second pharmacology model to the one or more separate devices; and
generating user interface data for a visualization panel portion displayable at the one or more separate devices, wherein rendered user interface data for the visualization panel portion at the one or more separate devices portrays one or more visualizations of respective medication concentration-versus-time plots resulting from one or more corresponding simulations of the optimized second pharmacology with respect to the patient-specific data and the one or more customized patient dosing regimens of the particular medication.

18. The system of claim 1, wherein feeding at least a portion of the first data set and the first pharmacology model into the predictive modeling framework to build at least one candidate according to one or more different types of machine learning models comprises:
  identifying, via the one or more different types of machine learning models, one or more new covariates as variables to be included in the at least one machine learning candidate model.

* * * * *